(12) United States Patent
Vogt

(10) Patent No.: US 6,896,705 B2
(45) Date of Patent: May 24, 2005

(54) MIXTURES OF SULFURIC ESTERS

(75) Inventor: Uwe Vogt, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/901,807

(22) Filed: Jul. 29, 2004

(65) Prior Publication Data

US 2005/0000041 A1 Jan. 6, 2005

Related U.S. Application Data

(62) Division of application No. 09/865,323, filed on May 25, 2001.

(30) Foreign Application Priority Data

Jun. 7, 2000 (DE) .......................... 100 28 224

(51) Int. Cl.$^7$ .................... C09B 67/00; C07C 305/08; C07C 305/12; C07C 305/20
(52) U.S. Cl. .................... 8/587; 8/576; 8/909; 8/917; 558/20; 558/41
(58) Field of Search .................... 558/20, 41; 8/576, 8/587, 909, 917

(56) References Cited

U.S. PATENT DOCUMENTS

| | | | |
|---|---|---|---|
| 2,353,500 A | * 7/1944 | Pyzel ......................... 558/42 |
| 3,684,427 A | 8/1972 | Walz et al. ..................... 8/26 |
| 3,740,345 A | 6/1973 | Berger ........................ 252/355 |
| 3,742,081 A | * 6/1973 | Goldsby ..................... 585/301 |
| 4,313,733 A | * 2/1982 | Zurbuchen et al. ............. 8/582 |
| 5,356,445 A | 10/1994 | De Meulemeester et al. ... 8/641 |
| 6,335,312 B1 | * 1/2002 | Coffindaffer et al. ....... 510/159 |

FOREIGN PATENT DOCUMENTS

| | | |
|---|---|---|
| DE | 19 40 178 A | 3/1971 |
| DE | 198 48 894 | 4/2000 |
| EP | 593 392 A | 4/1994 |

OTHER PUBLICATIONS

Scalia, "Reversed–phase high–performance liquid chromatographic method for the assay of 1,4–dioxane in sulphated polyoxyethylene alcohol surfactants" 1990, Journal of Pharmaceutical & Biomediacl Analysis vol. 8 p. os 8–12, pp 867–870.*

Wool Dyeing, Edited by D M Lewis, Professor, Department of Colour Chemistry & Dyeing, University of Leeds, Leeds. UK, p. 93, 1992 Society of Dyers and Colourists.

* cited by examiner

*Primary Examiner*—Margaret Einsmann
(74) *Attorney, Agent, or Firm*—Diderico van Eyl; Jennifer R. Seng; Jill Deresvich

(57) ABSTRACT

The invention relates to novel mixtures of sulfuric esters and specific sulfuric esters that are useful as leveling agents for the dyeing of nitrogenous fiber materials and to a process for their preparation by reacting sulfuryl chloride with specific alcohols.

5 Claims, No Drawings

MIXTURES OF SULFURIC ESTERS

This application is a Divisional of Ser. No. 09/865,323 filed May 25, 2001.

BACKGROUND OF THE INVENTION

The present invention relates to novel mixtures of sulfuric esters and specific sulfuric esters, processes for their preparation, and their use as dyeing auxiliaries.

Textiles are dyed using leveling agents as auxiliaries. These leveling agents are surface-active substances whose role is to efficiently wet the fiber or fiber blend to be dyed, to promote the penetration of the fibers by the dye, and to inhibit excessively rapid unlevel exhaustion of the dyes during the dyeing process. The use of leveling agents thus makes it possible to obtain an even and uniform dyeing result.

Nitrogenous fiber materials, especially wool, are suitably dyed with anionic dyes, for example, acid dyes, 1:1 metal complex dyes, 1:2 metal complex dyes, chromium dyes, or mixtures thereof.

The prior art discloses a wide variety of leveling agents for dyeing textile materials, especially wool, with the dyes mentioned. For example, the use of phosphoric esters is known (DE-A 16 19 372 and DE-A 19 46 058).

DE-A 19 40 178 discloses the use of polyalkoxylated ethanesulfonic acid compounds or their quaternization products as leveling agents for the dyeing of nitrogenous fiber materials with acid dyes or 1:2 metal complex dyes. The polyalkoxylated ethanesulfonic acid compounds in question have the following structural formula:

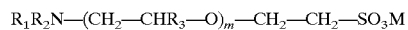

wherein
$R_1$ represents a $C_{12}$–$C_{22}$-alkyl, $C_{12}$–$C_{22}$-alkenyl, or $C_{12}$–$C_{22}$-cycloalkyl radical,
$R_2$ represents $CH_3$ or one of the groups —$(CH_2$—$CHR_3$—$O$—$)_n$H or —$(CH_2$—$CHR_3$—$O)_n$—$CH_2$—$CH_2$—$SO_3M$,
$R_3$ represents H, $CH_3$, $C_2H_5$, or phenyl,
M denotes a cation, and
the sum of m+n is 5 to 70, at least 80% of the alkylene oxide units in the molecule being ethylene oxide units.
EP-A 593,392 describes the use of compounds of the formula

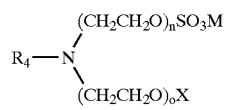

wherein
$R_4$ is a $C_{12}$–$C_{24}$-alkyl or alkenyl radical,
X is H or $SO_3M$,
M is H, alkali metal, or ammonium, and
n+o is 2 to 20,
as leveling auxiliaries in the dyeing of fiber materials composed of natural or synthetic polyamide in an aqueous liquor.

*Wool Dyeing* (Editor: D. M. Lewis; 1992, Society of Dyers and Colourists) similarly describes sulfated ethoxylated amines as amphoteric auxiliaries for dyeing wool.

It is an object of the present invention to provide novel substances useful as leveling agents in the dyeing of textile materials, especially wool.

SUMMARY OF THE INVENTION

This object is achieved by mixtures of sulfuric esters of the general formula (1)

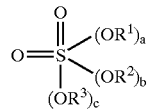

(1)

wherein
$R^1$ is an aliphatic radical having 1 to 30 carbon atoms,
$R^2$ is a radical of the general formula (2)

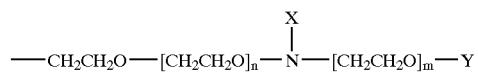

(2)

wherein
n is an integer from 0 to 30,
m is an integer from 1 to 29,
X is an aliphatic radical having 4 to 24 carbon atoms, and
Y is H or $SO_2(OM)$, where M represents hydrogen, alkali metal, ammonium, mono-, di-, tri-, or tetra($C_1$–$C_6$-alkyl)ammonium, or mono-, di-, tri-, or tetra($C_2$–$C_6$-alkanol)ammonium ions,
$R^3$ is a radical of the general formula (3)

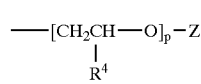

(3)

wherein
p is an integer from 4 to 35,
$R^4$ is H, methyl, ethyl, phenyl, or mixtures of H and methyl, and
Z is H, methyl, ethyl, or $SO_2(OM)$, where M represents hydrogen, alkali metal, ammonium, mono-, di-, tri-, or tetra-($C_1$–$C_6$-alkyl)ammonium, or mono-, di-, tri-, or tetra($C_2$–$C_6$-alkanol)ammonium ions, and
a, b, and c are identical or different and are 0, 1, or 2, with the proviso that a+b+c is 2,
obtainable by reacting sulfuryl chloride with a mixture of the alcohols $R^1OH$, $R^2OH$, and $R^3OH$, wherein $R^1$, $R^2$, and $R^3$ have the same meanings as for formula (1) except that Y is exclusively hydrogen and Z is either hydrogen, methyl, or ethyl.

DETAILED DESCRIPTION OF THE INVENTION

In the sulfuric esters of formula (1), $R^1$ is an aliphatic radical having 1 to 30 carbon atoms. This aliphatic radical is preferably a straight-chain or branched alkyl or alkenyl radical having 1 to 30 carbon atoms.

Examples of suitable straight-chain or branched $C_1$–$C_8$-alkyl groups are methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, 2-ethylhexyl, and n-octyl.

Examples of suitable straight-chain or branched $C_9$–$C_{30}$-alkyl groups are n-nonyl, isononyl, n-decyl, n-undecyl, n-dodecyl, n-tridecyl, n-tetra-decyl, n-pentadecyl, n-hexadecyl, n-heptadecyl, n-octadecyl, n-nonadecyl, n-eicosyl, and n-docosyl.

The meaning of alkenyl group for $R^1$ comprehends straight-chain and branched $C_1$–$C_{30}$-alkenyl groups having 1, 2, or 3 double bonds. Preferably they are straight-chain or branched $C_4$–$C_{30}$-alkenyl, especially $C_8$–$C_{20}$-alkenyl, groups. Examples of alkenyl groups are heptenyl, octenyl, nonenyl, decenyl, undecenyl, tridecenyl, tetradecenyl, pentadecenyl, hexadecenyl, heptadecenyl, octadecenyl, nonadecenyl, hexadecadienyl, hexadecatrienyl, octadecadienyl, and octadecatrienyl.

The meaning of alkyl or alkenyl for $R^1$ also comprehends mixtures of various alkyl or alkenyl groups as occur, for example, in natural fats and oils, for example, coconut oil, palm kernel oil, soya oil, colza oil, olive oil, sunflower oil, cottonseed oil, groundnut oil, linseed oil, rapeseed oil, or tallow fat.

Radical X in $R^2$ of the general formula (2) is an aliphatic radical having 4 to 24 carbon atoms. Useful aliphatic radicals are straight-chain and branched alkyl and alkenyl radicals having 4 to 24 carbon atoms, preferably 12 to 24 and particularly preferably 16 to 22 carbon atoms. More particularly, X is a dodecyl, tetradecyl, hexadecyl, octadecyl, eicosyl, docosyl, octadecenyl, or abietyl radical.

The meaning of alkyl or alkenyl for X likewise comprehends mixtures of various alkyl or alkenyl groups that occur, for example, in natural fats and oils, for example coconut oil, palm kernel oil, soya oil, colza oil, olive oil, sunflower oil, cottonseed oil, groundnut oil, linseed oil, rapeseed oil or tallow fat.

Radical Y in $R^2$ of the general formula (2) is H or $SO_2(OM)$. The cation M is hydrogen, alkali metal (preferably sodium or potassium), ammonium, mono-, di-, tri-, or tetra($C_1$–$C_6$-alkyl)ammonium, or mono-, di-, tri-, or tetra($C_2$–$C_6$-alkanol)ammonium ions. The latter are derived in particular from mono-, di-, or triethanolamine.

The index n in $R^2$ of the general formula (2) is an integer from 0 to 30, preferably from 0 to 10, especially from 0 to 5. The index m in $R^2$ of the general formula (2) is an integer from 1 to 29, preferably from 1 to 10, especially from 1 to 5.

Radical Z in $R^3$ of the general formula (3) is H, methyl, ethyl, or $SO_2(OM)$. Preferably, Z is H or SO(OM). The cation M is hydrogen, alkali metal (preferably sodium or potassium), ammonium, mono-, di-, tri-, or tetra($C_1$–$C_6$-alkyl)ammonium or mono-, di-, tri-, or tetra($C_2$–$C_6$-alkanol)-ammonium ions. The latter are derived in particular from mono-, di-, or triethanolamine.

$R^4$ in the general formula (3) is hydrogen, methyl, ethyl, or phenyl or else denotes mixtures of hydrogen and methyl. Preferably, $R^4$ is hydrogen or methyl. In the case of mixtures of hydrogen and methyl, not more than 80% of $R^4$ is methyl and not less than 20% of $R^4$ is hydrogen.

The index p in the general formula (3) is an integer from 4 to 35, preferably from 9 to 22.

Preference is given to mixtures of sulfuric esters of the general formula (1) in which
$R^1$ is an aliphatic radical having 4 to 30 carbon atoms,
$R^2$ is a radical of the general formula (2), where
   n is an integer from 0 to 10,
   m is an integer from 1 to 10,
   X is an aliphatic radical having 12 to 24 carbon atoms, and
   Y is H or $SO_2(OM)$, where M independently represents hydrogen, alkali metal, ammonium, mono-, di-, tri-, or tetra($C_1$–$C_6$-alkyl)ammonium, or mono-, di-, tri-, or tetra($C_2$–$C_6$-alkanol)ammonium ions,
$R^3$ is a radical of the general formula. (3) where
   p is an integer from 3 to 35,
   $R^4$ is H or methyl, and
   Z is H, methyl, ethyl, or $SO_2(OM)$, where M independently represents hydrogen, alkali metal, ammonium, mono-, di-, tri-, or tetra($C_1$–$C_6$-alkyl)ammonium, or mono-, di-, tri-, or tetra($C_2$–$C_6$-alkanol)ammonium ions, and
a, b, and c are identical or different and are 0, 1, or 2, with the proviso that a+b+c is 2.

Particular preference is given to mixtures of sulfuric esters of the general formula (1) where
$R^1$ is an aliphatic radical having 8 to 20 carbon atoms,
$R^2$ is a radical of the general formula (2) where
   n is an integer from 0 to 5,
   m is an integer from 1 to 5,
   X is an aliphatic radical having 16 to 22 carbon atoms, and
   Y is H,
$R^3$ is a radical of the general formula (3) where
   p is an integer from 9 to 22,
   $R^1$ is H, and
   Z is H, and
a, b, and c are identical or different and are 0, 1, or 2 with the proviso that a+b+c is 2.

The invention further provides a process for preparing the mixtures of sulfuric esters of the general formula (1) by reacting sulfuryl chloride with a mixture of the alcohols $R^1OH$, $R^2OH$, and $R^3OH$, where $R^1$, $R^2$, and $R^3$ in these alcohols have the meanings indicated for the general formula (1) except that Y is exclusively hydrogen and Z is either hydrogen, methyl, or ethyl.

In a suitable embodiment of the process according to the invention, a total of 3 mol of a mixture of the alcohols $R^1OH$, $R^2OH$, and $R^3OH$ is reacted with 1.5 to 2.5 mol (preferably 1.5 to 1.8 mol) of sulfuryl chloride.

The three alcohols $R^1OH$, $R^2OH$, and $R^3OH$ can be used in the following quantity ratios:
$R^1OH$ 10 to 40 (preferably 30 to 40) mol %
$R^2OH$ 20 to 80 (preferably 30 to 40) mol %, and
$R^3OH$ 10 to 40 (preferably 30 to 40) mol %,
the amounts of the three alcohols always totaling 100 mol %.

It is customary to initially charge the alcohols $R^1OH$, $R^2OH$, and $R^3OH$, to heat this mixture to melt the alcohols, and to add the sulfuryl chloride at 40 to 60° C. This addition is accompanied by an increase in the temperature, generally to not less than 80° C. Subsequently the reaction mixture is stirred at elevated temperature, preferably about 100° C. By reducing the pressure it is possible to remove the HCl of reaction from the reaction product. It is further advantageous to subsequently add a base such as aqueous sodium hydroxide solution or diethanolamine to set a pH of 5 to 7.

The $R^1OH$ alcohols are generally available. The $R^2OH$ alcohols can be prepared according to methods known to those skilled in the art, for example, as described in DE-A 1 940 178. Initially 2 to 60 mol of ethylene oxide are added to an aliphatic amine X—$NH_2$, where X is as defined above. Useful aliphatic amines are in particular dodecyl-, tetradecyl-, hexadecyl-, octadecyl-, eicosyl-, docosyl-, octadecenyl-, or abietylamine. Preferred examples further include reaction products of 1 mol of tallow fatty amine with 2 mol, 5 mol, or 10 mol of ethylene oxide.

The esterification of the terminal OH group in the $R^2$ radical, so that Y is subsequently $SO_2$ (OM), is possible in the course of the reaction of the alcohols with sulfuryl chloride, provided that an excess of sulfuryl chloride is used.

The R³OH alcohols are generally available. Preferred examples of R³OH are triethylene glycol and polyethylene glycols having average molecular weights of 200 to 1500 g/mol or monomethyl or monoethyl ethers of these compounds.

The esterification of the terminal OH group in the R³ radical, so that Z is subsequently $SO_2(OM)$, is possible in the course of the reaction of the alcohols with sulfuryl chloride, provided that an excess of sulfuryl chloride is used.

It will be appreciated that any other preparative methods known to those skilled in the art are suitable, as long as they lead to the inventive mixtures of sulfuric esters of the general formula (1).

The reaction product that forms in the course of the reaction according to the invention is a mixture of various sulfuric esters of the general formula (1). If desired, it is also possible to separate individual sulfuric esters out of these mixtures by suitable methods known to those skilled in the art.

The invention also provides specific sulfuric esters of the general formula (1) where
$R^1$, $R^2$, and $R^3$ have the meanings mentioned for the inventive mixtures of the sulfuric esters, and
a, b, and c are identical or different and are 0 or 1, with the proviso that a+b+c is 2.

Preference is given to those sulfuric esters of the general formula (1) where
$R^1$, $R^2$, and $R^3$ have the meanings mentioned for the preferred mixtures of the sulfuric esters, and
a, b, and c are identical or different and are 0 or 1, with the proviso that a+b+c is 2.

Particular preference is given to those sulfuric esters of the general formula (1) where
$R^1$, $R^2$, and $R^3$ have the meanings mentioned for the particularly preferred mixtures of the sulfuric esters, and
a, b, and c are identical or different and are 0 or 1, with the proviso that a+b+c is 2.

The inventive mixtures of the sulfuric esters of formula (1) and the specific sulfuric esters defined above are generally in solid, waxy form at room temperature. They start to melt in the range from 30 to 60° C. To convert these mixtures of sulfuric esters or the specific sulfuric esters into a liquid form because it is more convenient to meter in that form, it is advisable to prepare organic or aqueous-organic formulations.

The invention accordingly further provides organic or aqueous-organic formulations including 25–70% by weight of the mixtures of the sulfuric esters of the general formula (1) or of the specific above-defined sulfuric esters. Useful organic solvents are inert with regard to the sulfuric esters and water-miscible. Preference is given to the use of mono-, di-, or oligoethylene glycols, -propylene glycols, or -ethylene/propylene glycols, their mono- or diethers or mixtures thereof, especially butyldiglycol or methyldiglycol. The formulations of the mixtures of the sulfuric esters of the general formula (1) can be prepared using the reaction mixture of the process according to the invention without further work-up.

The invention further provides for the use of the mixtures of the sulfuric esters of formula (1) or of the specific sulfuric esters defined above or of the respective organic or aqueous-organic formulations as dyeing auxiliaries in the dyeing of nitrogenous fiber materials, preferably wool.

The mixtures of the sulfuric esters of the general formula (1) or the specific sulfuric esters defined above or their respective organic or aqueous-organic formulations are added to the dyeing liquors. The dyeing of nitrogenous textile materials, especially wool, in the presence of the inventive mixtures of the sulfuric esters of formula (1) or of the specific sulfuric esters defined above can be carried out by initially introducing the material to be dyed into a hot dyeing liquor at 40 to 50° C. that contains the dye, the mixtures of the sulfuric esters of the general formula (1) or the specific sulfuric esters defined above, and acids, for example, acetic acid. The dyebath is then gradually heated to 100 to 130° C. and maintained at that temperature until it is exhausted. It is likewise possible to pretreat the textile material at 40 to 50° C. for a short time in aqueous liquor containing only the mixture of the sulfuric esters of formula (1) or the specific sulfuric esters and acid and only then to add the dyes to this liquor at temperatures between 40 to 98° C. and subsequently to gradually increase the temperature of the dyebath to 100 to 130° C. and to maintain that temperature until it is exhausted.

Useful dyes include anionic dyes suitable for dyeing nitrogenous fiber materials, especially wool, for example, acid dyes, 1:1 metal complex dyes, 1:2 metal complex dyes, or chrome dyes and also mixtures thereof.

The amounts in which the inventive mixtures or the specific sulfuric esters are added to the dyebaths can vary within wide limits. The amounts are readily ascertainable by preliminary experimentation. Useful amounts generally range from 0.25 to 3.0% (preferably from 0.5 to 1.0%) of the weight of the material to be dyed.

The dyeing process is useful for all nitrogenous fiber materials that are dyeable with the dyes mentioned, especially for natural polyamides, such as wool and silk, for synthetic polyamides, such as hexamethylene diadipate, poly-ε-caprolactam and poly-ω-aminoundecanoic acid, for cationically modified polyacrylonitriles, and also their mixtures with each other or with other fiber materials, such as fiber materials composed of natural and regenerated cellulose, polyacrylonitrile, polyurethanes, or polyesters. The dyeable fiber materials mentioned can be present in a wide variety of processing forms, for example, as staple, top, textured threads, tow, yarn, wovens, knits, or nonwovens.

The inventive mixtures of the sulfuric esters of the general formula (1) and of the specific sulfuric esters defined above provide very uniform dyeing of these nitrogenous textile materials. In addition to their outstanding quality as dyeing auxiliaries, the mixtures of the sulfuric esters of the general formula (1) and also the specific sulfuric esters are surprisingly also readily biodegradable.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Example 1 (Preparation of an Inventive Mixture of Sulfuric Esters)

A mixture of 27.0 g (0.1 mol) of stearyl alcohol, 40.0 g (0.1 mol) of polyethylene glycol having an average molecular weight of 400, and 48.8 g (0.1 mol) of a reaction product of 1 mol of tallow fatty amine with 5 mol of ethylene oxide was initially charged at 55° C. and admixed with 20.2 g (0.15 mol) of sulfuryl chloride over 10 min, during which time the temperature rose to 90° C. The batch was subsequently stirred at 100° C. for 4 hours under a slow stream of nitrogen, followed by a further hour of stirring under a reduced pressure of 20 mbar. The batch was cooled down to 50° C. and adjusted by careful addition of 45% strength aqueous sodium peroxide solution to a pH of 5–6. After cooling down to room temperature, the reaction product solidified into a waxy mass.

Example 2 (Preparation of an Inventive Mixture of Sulfuric Esters)

Example 1 was repeated, except that diethanolamine was used to neutralize the batch instead of aqueous sodium hydroxide solution. This furnished a waxy mass on cooling.

Example 3 (Preparation of an Inventive Mixture of Sulfuric Esters)

Example 1 was repeated, except that the neutralizing was omitted. This afforded a waxy mass that, when dissolved in distilled water to form a 5% solution, had a pH of 2.8.

Example 4 (Preparation of an Inventive Mixture of Sulfuric Esters)

Example 1 was repeated to react 24.2 g (0.1 mol) of hexadecyl alcohol, 40.0 g (0.1 mol) of polyethylene glycol having an average molecular weight of 400, and 48.8 g (0.1 mol) of a reaction product of 1 mol of tallow fatty amine with 5 mol of ethylene oxide. A waxy product was obtained on cooling.

Example 5 (Preparation of an Inventive Mixture of Sulfuric Esters)

Example 4 was repeated, except that diethanolamine was used to neutralize the batch instead of aqueous sodium hydroxide solution. This likewise furnished a waxy mass.

Example 6 (Preparation of a Liquid Formulation of the Mixture of Sulfuric Esters of Example 2)

100 g of the inventive mixture of Example 2 were stirred with 100 g of butyl diglycol at 50° C. until a clear solution was obtained. This was followed by cooling.

Example 7 (Preparation of a Liquid Formulation of the Mixture of Sulfuric Esters of Example 5)

30 g of the inventive mixture of Example 5 were stirred with 40 g of butyldiglycol and 30 g of demineralized water at 50° C. until a clear solution was obtained. This was followed by cooling.

Example 8 (Use)

30 g of worsted wool yarn were dyed as follows (percentages were on weight of fiber; ISOLAN® dyes were from DyStar Deutschland GmbH & Co. KG) in a circulation dyeing machine (Color Star from Mathis):

1. Dyeing

| Liquor circulation: | Alternately 4 min in to out and 2 min out to in | |
| --- | --- | --- |
| Liquor: | ISOLAN Yellow K-GLN 250% | 0.3% |
| | ISOLAN Bordo R 220% | 0.15% |
| | ISOLAN Grey K-BRLS 200% | 0.3% |
| | Sodium sulfate | 5% |
| | Acetic acid 60% | 3% |
| | Mixture per Example 1 | 0.5% |
| pH of liquor: | 4.5 | |
| Liquor ratio: | 20:1 | |
| Starting temperature: | 50° C. | |
| 10 min prerun at 50° C. | | |
| heating to 98° C. (heating rate 2° C./min) | | |
| maintain at 98° C. for 30 min | | |
| cool to 70° C. (cooling rate 2° C./min) | | |

-continued

| maintain at 70° C. for 5 min | |
| --- | --- |
| drop the liquor | |

2. Rinsing

| Liquor circulation: | Alternately 4 min in to out and 2 min out to in |
| --- | --- |
| Temperature: | 40° C. |
| Rinse time: | 12 min |
| drop rinse liquor | |
| add new rinse liquor | |
| Temperature: | 60° C. |
| Rinse time: | 12 min |
| drop rinse liquor | |

3. Hydroextraction and Drying of Worsted Yarn Package 12 hours at 50° C.

The dyed worsted wool yarn was knitted up inside-middle-outside. The knitted piece was assessed for the hue profile, i.e., the differences in hue between the inside, middle and outside regions of the yarn package. The knitted piece was observed to have an impeccable hue profile.

Example 9 (Use)

Example 8 was repeated with the following liquor:

| ISOLAN Yellow S-GL | 0.3% |
| --- | --- |
| ISOLAN Red S-RL | 0.3% |
| ISOLAN Grey S-GL | 0.3% |
| Sodium sulfate | 5% |
| Acetic acid 60% | 3% |
| Mixture as per Example 5 | 0.5% | likewise afforded a knitted piece having an impeccable hue profile.

Examples 10 and 11

Comparison

The dyeing described in Examples 8 and 9 was conducted without the inventive mixture of sulfuric esters as auxiliary resulted in the dyed worsted wool yarn giving rise to a knitted piece which exhibited a very distinct inside-middle-outside effect, i.e., a pronounced hue difference within the knitted piece.

What is claimed is:

1. A sulfuric ester of formula (1)

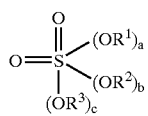

(1)

wherein

R$^1$ is an aliphatic radical having 1 to 30 carbon atoms,
R$^2$ is a radical of formula (2)

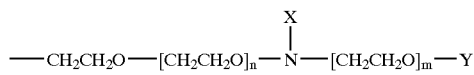  (2)

wherein
n is an integer from 0 to 30,
m is an integer from 1 to 29,
X is an aliphatic radical having 4 to 24 carbon atoms, and
Y is H or SO$_2$(OM), where M represents hydrogen, alkali metal, ammonium, mono-, di-, tri-, or tetra(C$_1$–C$_6$-alkyl)ammonium, or mono-, di-, tri-, or tetra(C$_2$–C$_6$-alkanol)ammonium ions, R$^3$ is a radical of formula (3)

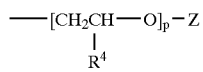  (3)

wherein
p is an integer from 4 to 35,
R$^4$ is H, methyl, ethyl, phenyl, or mixtures of H and methyl, and
Z is H, methyl, ethyl, or SO$_2$(OM), where M represents hydrogen, alkali metal, ammonium, mono-, di-, tri-, or tetra(C$_1$–C$_6$-alkyl)ammonium, or mono-, di-, tri-, or tetra(C$_2$–C$_6$-alkanol)ammonium ions, and
a, b, and c are identical or different and are 0 or 1, with the proviso that a+b+c is 2.

2. A sulfuric ester according to claim 7 wherein
R$^1$ is an aliphatic radical having 4 to 30 carbon atoms,
R$^2$ is a radical of formula (2)

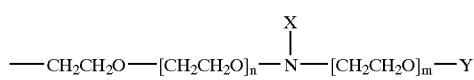  (2)

wherein
n is an integer from 0 to 10,
m is an integer from 1 to 10,
X is an aliphatic radical having 12 to 24 carbon atoms, and
Y is H or SO$_2$(OM), where M independently represents hydrogen, alkali metal, ammonium, mono-, di-, tri-, or tetra(C$_1$–C$_6$-alkyl)ammonium, or mono-, di-, tri-, or tetra(C$_2$–C$_6$-alkanol)ammonium ions, R$^3$ is a radical of formula (3)

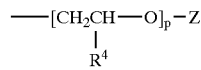  (3)

wherein
p is an integer from 3 to 35,
R$^4$ is H or methyl, and
Z is H, methyl, ethyl, or SO$_2$(OM), where M independently represents hydrogen, alkali metal, ammonium, mono-, di-, tri-, or tetra(C$_1$–C$_6$-alkyl)ammonium, or mono-, di-, tri-, or tetra(C$_2$–C$_6$-alkanol)ammonium ions, and
a, b, and c are identical or different and are 0 or 1, with the proviso that a+b+c is 2.

3. A sulfuric ester according to claim 7 wherein
R$^1$ is an aliphatic radical having 8 to 20 carbon atoms,
R$^2$ is a radical of formula (2)

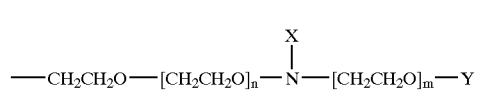  (2)

wherein
n is an integer from 0 to 5,
m is an integer from 1 to 5,
X is an aliphatic radical having 16 to 22 carbon atoms, and
Y is H,
R$^3$ is a radical of formula (3)

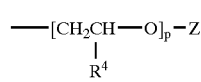  (3)

wherein
p is an integer from 9 to 22,
R$^1$ is H, and
Z is H, and
a, b, and c are identical or different and are 0 or 1, with the proviso that a+b+c is 2.

4. An organic or aqueous-organic formulation comprising 25 to 70% by weight of a mixture of sulfuric esters according to claim 7.

5. An organic or aqueous-organic formulation according to claim 4 wherein the organic component of the formulation comprises one or more organic solvents selected from the group consisting of mono-, di-, and oligoethylene glycols, oligopropylene glycols, and oligoethylene/propylene glycols, and mono- and diethers thereof.

* * * * *